US009884848B2

(12) United States Patent
Larsen et al.

(10) Patent No.: US 9,884,848 B2
(45) Date of Patent: *Feb. 6, 2018

(54) PHENYL TRIAZOLE DERIVATIVE AND ITS USE FOR MODULATING THE GABA$_A$ RECEPTOR COMPLEX

(71) Applicant: SANIONA A/S, Ballerup (DK)

(72) Inventors: Janus Schreiber Larsen, Ballerup (DK); Magnus Gustafsson, Ballerup (DK); Carsten Jessen, Ballerup (DK)

(73) Assignee: Saniona A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/290,480

(22) Filed: Oct. 11, 2016

(65) Prior Publication Data

US 2017/0114045 A1 Apr. 27, 2017

Related U.S. Application Data

(63) Continuation of application No. 14/411,326, filed as application No. PCT/EP2013/063194 on Jun. 25, 2013, now Pat. No. 9,475,797.

(60) Provisional application No. 61/664,288, filed on Jun. 26, 2012.

(30) Foreign Application Priority Data

Jun. 26, 2012 (DK) ................................ 2012 70369

(51) Int. Cl.
*C07D 403/12* (2006.01)
*A61K 31/415* (2006.01)
*A01N 43/56* (2006.01)

(52) U.S. Cl.
CPC .................................. *C07D 403/12* (2013.01)

(58) Field of Classification Search
None
See application file for complete search history.

(56) References Cited

U.S. PATENT DOCUMENTS

| 6,743,798 B1 | 6/2004 | Straub et al. |
| 7,091,346 B1 | 8/2006 | Zimmermann et al. |
| 7,176,312 B2 | 2/2007 | Ding et al. |
| 2002/0068721 A1 | 6/2002 | Weigele et al. |
| 2003/0139427 A1 | 7/2003 | Castelhano et al. |
| 2003/0229105 A1 | 12/2003 | Kashanchi |
| 2004/0116376 A1 | 6/2004 | Elzein et al. |
| 2005/0124637 A1 | 6/2005 | Chang et al. |
| 2005/0165029 A1 | 7/2005 | Patel et al. |
| 2005/0187389 A1 | 8/2005 | Milanov et al. |
| 2005/0288503 A1 | 12/2005 | Adams et al. |
| 2006/0009642 A1 | 1/2006 | Ding et al. |
| 2007/0249639 A1 | 10/2007 | Baenteli et al. |
| 2007/0275986 A1 | 11/2007 | Becq et al. |
| 2008/0242683 A1 | 10/2008 | Fairhurst et al. |
| 2008/0275045 A1 | 11/2008 | Eriksen et al. |
| 2009/0030019 A1 | 1/2009 | Meijer et al. |
| 2009/0036475 A1 | 2/2009 | Eriksen et al. |
| 2009/0306102 A1 | 12/2009 | Eriksen et al. |
| 2010/0035934 A1 | 2/2010 | Eriksen et al. |
| 2010/0056494 A1 | 3/2010 | Winzeler et al. |
| 2010/0105705 A1 | 4/2010 | Eriksen et al. |
| 2010/0130516 A1 | 5/2010 | Eriksen et al. |
| 2010/0152210 A1 | 6/2010 | Eriksen et al. |
| 2010/0183564 A1 | 7/2010 | Boitano et al. |
| 2010/0197914 A1 | 8/2010 | Fairhurst |
| 2011/0144140 A1 | 6/2011 | Eriksen et al. |
| 2011/0237607 A1 | 9/2011 | Eriksen et al. |
| 2011/0251217 A1 | 10/2011 | Eriksen et al. |
| 2012/0004246 A1 | 1/2012 | Eriksen et al. |

FOREIGN PATENT DOCUMENTS

| EP | 1724268 A1 | 11/2006 |
| WO | WO 97/16452 A1 | 5/1997 |
| WO | WO 97/20842 A1 | 6/1997 |
| WO | WO 99/32454 A1 | 7/1999 |
| WO | WO 2001/44259 A1 | 6/2001 |
| WO | WO 2001/44260 A2 | 6/2001 |
| WO | WO 03/002565 A1 | 1/2003 |
| WO | WO 2003/014137 A1 | 2/2003 |
| WO | WO 03/031406 A2 | 4/2003 |
| WO | WO 2004/021979 A2 | 3/2004 |
| WO | WO 2005/080377 A1 | 9/2005 |
| WO | WO 2006/074925 A1 | 7/2006 |
| WO | WO 2006/097260 A1 | 9/2006 |
| WO | WO 2006/125211 A1 | 11/2006 |
| WO | WO 2007/039389 A1 | 4/2007 |
| WO | WO 2007/042420 A1 | 4/2007 |
| WO | WO 2007/054444 A2 | 5/2007 |
| WO | WO 2007/071598 A1 | 6/2007 |
| WO | WO 2007/074078 A2 | 7/2007 |
| WO | WO 2007/074089 A1 | 7/2007 |
| WO | WO 2007/137954 A1 | 12/2007 |
| WO | WO 2008/025539 A1 | 3/2008 |
| WO | WO 2008/025540 A1 | 3/2008 |
| WO | WO 2008/040753 A1 | 4/2008 |
| WO | WO 2009/000662 A1 | 12/2008 |
| WO | WO 2009/071464 A1 | 6/2009 |
| WO | WO 2009/071476 A1 | 6/2009 |
| WO | WO 2009/071477 A1 | 6/2009 |
| WO | WO 2009/149795 A2 | 12/2009 |

(Continued)

OTHER PUBLICATIONS

Brown et al., "Heterocyclic Amplifiers of Phleomycin. VI Some Phenylpurines, Phenylpteridines, Phenylquinazolines and Related Compounds", Australian Journal of Chemistry, Jan. 1, 1985, vol. 38, 467-474.

(Continued)

*Primary Examiner* — Kortney L Klinkel
*Assistant Examiner* — Tori M Strong
(74) *Attorney, Agent, or Firm* — Baker & Hostetler LLP

(57) ABSTRACT

This invention relates to a novel phenyl triazole derivative, pharmaceutical compositions containing this compound, and methods of treatment therewith. The compound of the invention is in particular considered useful for the treatment of central nervous system diseases and disorders which are responsive to modulation of GABA$_A$ receptors containing the α5 subunit.

6 Claims, 1 Drawing Sheet

(56) References Cited

FOREIGN PATENT DOCUMENTS

| WO | WO 2010/097368 A1 | 9/2010 |
|---|---|---|
| WO | WO 2010/112475 A1 | 10/2010 |
| WO | WO 2010/125042 A1 | 11/2010 |
| WO | WO 2010/127968 A1 | 11/2010 |
| WO | WO 2010/127974 A1 | 11/2010 |
| WO | WO 2010/127975 A1 | 11/2010 |
| WO | WO 2010/127976 A1 | 11/2010 |
| WO | WO 2010/127978 A1 | 11/2010 |
| WO | WO 2011/020615 A1 | 2/2011 |
| WO | WO 2012/062687 A1 | 5/2012 |
| WO | WO 2012/076590 A1 | 6/2012 |

OTHER PUBLICATIONS

Jacobs et al., "Substituted 2, 4-Diaminoquinazolines and 2,4-Diamino-8-Alkylpurines as Antagonists of the Neurokinin-2 ($NK_2$) Receptor", Boorganic & Medicianl Chemistry letters, Dec. 1995, vol. 5, No. 23, 2879-2884.

Mirza et al., "NS11394 [3'[5-(1-Hydroxy-1-Methyl-Ethyl)-Benzoimidazol-1-Yl]-Biphenyl-2-Carbonitrile], a Unique Subtype-Selective $GABA_A$ Receptor Positive Allosteric Modulator: In Vitro Actions, Pharmacokinetic Properties and in Vivo Anxiolytic Efficacy", The Journal of Pharmacology and Experimental Therapeutics, Sep. 2008, 327, 954-968.

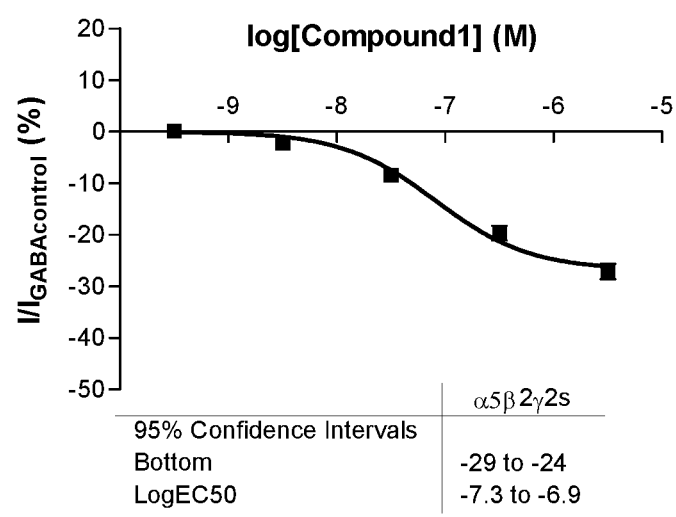

PHENYL TRIAZOLE DERIVATIVE AND ITS USE FOR MODULATING THE GABA$_A$ RECEPTOR COMPLEX

CROSS REFERENCE TO RELATED APPLICATIONS

This application is a continuation of U.S. application Ser. No. 14/411,326, filed Dec. 24, 2014, which is the National Stage Entry of International Application No. PCT/EP2013/063194, filed Jun. 25, 2013, which claims the benefit of U.S. Provisional Application No. 61/664,288, filed Jun. 26, 2012, and Denmark Application No. PA2012 70369, filed Jun. 26, 2012, the entireties of which are incorporated herein by reference.

TECHNICAL FIELD

This invention relates to a novel phenyl triazole derivative, pharmaceutical compositions containing this compound, and methods of treatment therewith. The compound of the invention is in particular considered useful for the treatment of central nervous system diseases and disorders which are responsive to modulation of GABA$_A$ receptors containing the α5 subunit.

BACKGROUND ART

The GABA$_A$ receptor protein complex is the molecular target of a number of ligands, including the benzodiazepine class of tranquilizer drugs. Multiple isoforms of the GABA$_A$ receptor exist; each receptor is a pentameric complex comprising subunits drawn from $\alpha_{1-6}$, $\beta_{1-3}$, $\gamma_{1-3}$, δ, ε, and θ subunit isoforms. However, the classical benzodiazepines show no subtype selectivity. Moreover it is believed that one of the key elements responsible for the drawbacks of the classical benzodiazepanes (such as sedation, dependency and cognitive impairment) has to do with the α1 subunit of the GABA$_A$ receptors.

Further, it has been suggested that the GABA$_A$ α5 subunit represents a therapeutic target for treatment of various diseases and disorders of the central nervous system, and literature has establish a nexus between the GABA$_A$ α5 subunit as therapeutic target, and various acute and chronic neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis, dementia caused by AIDS, psychotic disorders, substance-induced psychotic disorder, anxiety disorders, generalized anxiety disorder, panic disorder, delusional disorder, obsessive compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit hyperactivity disorder, neuropathic pain, stroke, attentional disorders, eating disorders, anorexia, anorexia nervosa, cachexia, weight loss, muscle atrophy, pain conditions, chronic pain, nociceptive pain, post-operative pain, osteoarthritis pain, rheumatoid arthritis pain, musculoskeletal pain, burn pain, ocular pain, pain due to inflammation, pain due to bone fracture, hyperalgesia, neuropathic pain, herpes-related pain, HIV-related neuropathic pain, traumatic nerve injury, post-stroke pain, post-ischemia pain, fibromyalgia, chronic headache, migraine, tension-type headache, diabetic neuropathic pain, phantom limb pain, visceral pain and cutaneous pain, and compounds capable of modulating GABA$_A$ receptors containing the α5 subunit are in particular expected to be useful candidates for the treatment of i.a. cognitive disorders, Alzheimer's disease, schizophrenia, positive, negative and/or cognitive symptoms associated with schizophrenia, and cognitive deficits associated with Down syndrome, with autism, with neurofibromatosis type I, or after stroke.

Isoxazole derivatives capable of modulating the GABA$_A$ receptor complex are known from e.g. WO 2007/039389, WO 2007/042420, WO 2007/054444, WO 2007/071598, WO 2007/074078, WO 2007/074089, WO 2007/137954, WO 2009/000662, WO 2009/071464, WO 2009/071476, WO 2009/071477, WO 2010/097368, WO 2010/112475, WO 2010/125042, WO 2010/127968, WO 2010/127974, WO 2010/127975, WO 2010/127976 and WO 2010/127978, and triazole derivatives capable of modulating the GABA$_A$ receptor complex are known from e.g. WO 2012/062687. Moreover WO 2008/025539, WO 2008/025540, WO 2009/149795 and WO 2011/020615 describe heterocyclic compounds, including certain phenyl triazole derivatives, useful as agonists of the NR1 H4 (FXR) receptor. However, the triazole derivatives of the present invention have not been reported.

SUMMARY OF THE INVENTION

In its first aspect, the invention provides a phenyl triazole derivative of the following structure (I):

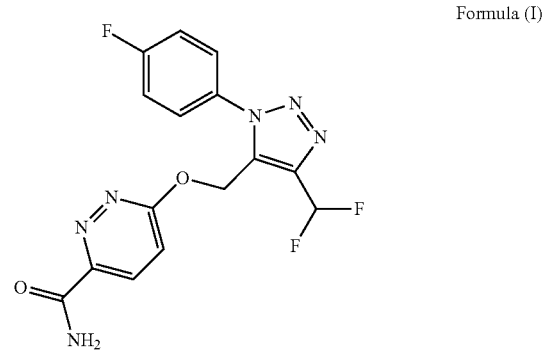 [SMILES: NC(=O)c1ccc(OCc2c(C(F)F)nnn2-c2ccc(F)cc2)nn1]

Formula (I)

i.e. 6-[[5-(difluoromethyl)-3-(4-fluorophenyl)triazol-4-yl]methoxy]pyridazine-3-carboxamide, and pharmaceutically acceptable salts thereof.

In its second aspect, the invention provides a pharmaceutical composition, comprising a therapeutically effective amount of the phenyl triazole derivative of formula (I) of the invention, or a pharmaceutically acceptable salt thereof, together with at least one pharmaceutically acceptable carrier, excipient or diluent.

In a further aspect, the invention relates to the use of the phenyl triazole derivative of formula (I) of the invention, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of GABA$_A$ receptors containing the α5 subunit.

In a still further aspect, the invention provides a method for treatment, prevention or alleviation of a disease or a disorder or a condition of a living animal body, including a human, which disorder, disease or condition is responsive to modulation of GABA$_A$ receptors containing the α5 subunit, which method comprises the step of administering to such a living animal body in need thereof a therapeutically effective amount of the phenyl triazole derivative of formula (I) of the invention, or a pharmaceutically acceptable salt thereof.

Other objects of the invention will be apparent to the person skilled in the art from the following detailed description and examples.

BRIEF DESCRIPTION OF THE DRAWING

FIG. 1 shows modulation of α$_5$β$_2$γ$_2$ GABA$_A$ receptor currents by the compound of formula (I) in *Xenopus laevis* oocytes.

DETAILED DISCLOSURE OF THE INVENTION

Phenyl Triazole Derivatives

In its first aspect the present invention provides a phenyl triazole derivative of formula (I) of the following structure:

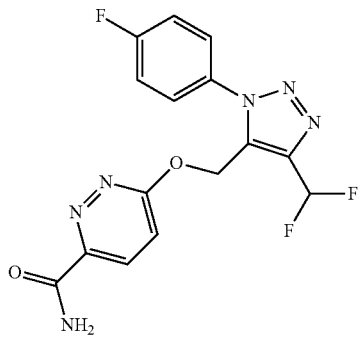 [SMILES: NC(=O)c1ccc(OCc2c(C(F)F)nnn2-c2ccc(F)cc2)nn1]

i.e. 6-[[5-(difluoromethyl)-3-(4-fluorophenyl)triazol-4-yl]methoxy]-pyridazine-3-carboxamide, and pharmaceutically acceptable salts thereof.

Pharmaceutically Acceptable Salts

The phenyl triazole derivative of formula (I) of the invention may be provided in any form suitable for the intended administration. Suitable forms include pharmaceutically (i.e. physiologically) acceptable salts of the compound of the invention.

Examples of pharmaceutically acceptable salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Such pharmaceutically acceptable salts and common methodology for preparing them are known in the art. Further details may be found in Stahl P et al, *Handbook of Pharmaceutical Salts: Properties, Selection and Use*; Wiley-VCH, 2002.

In addition, the phenyl triazole derivative of formula (I) of the invention may exist in the form of a polymorph, or the compound may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Labelled Compounds

The phenyl triazole derivative of formula (I) of the invention may be used in its labelled or unlabelled form. In the context of this invention a labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Deuterated Analogs

The phenyl triazole derivative of formula (I) of the invention may be provided in the form of their deuterated analogs. Deuterium forms bonds with carbon that vibrate at a lower frequency and are thus stronger than C—H bonds. Therefore "heavy hydrogen" (deuterium) versions of drugs may be more stable towards degradation and last longer in the organism.

Methods of Preparation

The phenyl triazole derivative of formula (I) of the invention may be prepared by conventional methods for chemical synthesis, e.g. those described in the working examples. The starting materials for the process described in the present application are known or may readily be prepared by conventional methods from commercially available chemicals.

The end product of the reactions described herein may be isolated by conventional techniques, e.g. by extraction, crystallisation, distillation, chromatography, etc.

Biological Activity

The phenyl triazole derivative of formula (I) of the invention are capable of modulating $GABA_A$ receptors containing the α5 subunit. Thus in further aspect, the phenyl triazole derivative of formula (I) of the invention is considered useful for the treatment, prevention or alleviation of a disease, disorder or condition responsive to modulation of $GABA_A$ receptors containing the α5 subunit, in particular in the central nervous system.

In one embodiment, the phenyl triazole derivative of formula (I) of the invention is considered useful for the treatment, prevention or alleviation of a disease, disorder or condition which is selected from the group of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit hyperactivity disorder, neuropathic pain, stroke, attentional disorders, and for use as cognitive enhancers.

In another embodiment, the phenyl triazole derivative of formula (I) of the invention is considered useful for the treatment, prevention or alleviation of a disease, disorder or condition which is selected from the group of eating disorders, anorexia, anorexia nervosa, cachexia, weight loss, muscle atrophy, pain conditions, chronic pain, nociceptive pain, post-operative pain, osteoarthritis pain, rheumatoid arthritis pain, musculoskeletal pain, burn pain, ocular pain, pain due to inflammation, pain due to bone fracture, hyperalgesia, neuropathic pain, herpes-related pain, HIV-related neuropathic pain, traumatic nerve injury, post-stroke pain, post-ischemia pain, fibromyalgia, chronic headache, migraine, tension-type headache, diabetic neuropathic pain, phantom limb pain, visceral pain and cutaneous pain.

In a third embodiment, the phenyl triazole derivative of formula (I) of the invention is considered useful for the treatment, prevention or alleviation of a disease, disorder or condition selected from the group of cognitive disorders, Alzheimer's disease, schizophrenia, positive, negative and/or cognitive symptoms associated with schizophrenia, and cognitive deficits associated with Down syndrome, with autism, with neurofibromatosis type I, or after stroke.

In a fourth embodiment, the phenyl triazole derivative of formula (I) of the invention is considered useful for the treatment, prevention or alleviation of a disease, disorder or condition selected from the group of Alzheimer's disease, schizophrenia and Down syndrome.

In a fifth embodiment, the phenyl triazole derivative of formula (I) of the invention is considered useful as a cognitive enhancer.

Further, the phenyl triazole derivative of formula (I) of the invention may be useful as a radioligand in assays for detecting compounds capable of modulating $GABA_A$ receptors containing the α5 subunit.

It is at present contemplated that a suitable dosage of the active pharmaceutical ingredient (API), that is the compound of formula (I) or a pharmaceutically acceptable salt thereof, including solvates and anhydrates, is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Pharmaceutical Compositions

In another aspect the invention provides novel pharmaceutical compositions comprising a therapeutically effective amount of the phenyl triazole derivative of formula (I) of the invention.

While the phenyl triazole derivative of formula (I) of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the phenyl triazole derivative of formula (I) of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The phenyl triazole derivative of formula (I) of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The phenyl triazole derivative of formula (I) of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from a phenyl triazole derivative of formula (I) of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, cellulose, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

In one embodiment, the invention provides tablets or capsules for oral administration.

In another embodiment, the invention provides liquids for intravenous administration and continuous infusion.

Further details on techniques for formulation and administration may be found in the latest edition of *Remington's Pharmaceutical Sciences* (Maack Publishing Co., Easton, Pa.).

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of $GABA_A$ receptors containing the α5 subunit, and which method comprises administering to such a living animal body, including a human, in need thereof an effective amount of the phenyl triazole derivative of formula (I) of the invention, or a pharmaceutically acceptable salt thereof It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparative Example

Preparation of 6-[[5-(difluoromethyl)-3-(4-fluorophenyl)triazol-4-yl]methoxy]-pyridazine-3-carboxamide (Compound 1)

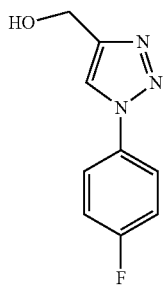 [SMILES: OCc1cn(-c2ccc(F)cc2)nn1]

[1-(4-fluorophenyl)triazol-4-yl]methanol

1-Azido-4-fluorobenzene (8.90 g, 61.7 mmol) and propargyl alcohol (4.15 g, 74.0 mmol) were dissolved in tert-butanol (90 mL) and water (90 mL). Copper(II)sulphate pentahydrate (1.54 g, 6.17 mmol) and L-ascorbic acid sodium salt (1.22 g, 6.17 mmol) were added and the mixture was stirred at room temperature. After 2 hours the mixture was poured into water (700 mL) and the formed precipitate was collected by filtration (8.45 g, 71%, brownish solid)). The aqueous phase was extracted with ethyl acetate (2×100 mL) and the combined organic phases were dried ($MgSO_4$) and evaporated to obtain a second batch of the desired product (3.1 g, 26%, brownish solid).

$^1$H NMR (400 MHz, DMSO) 8.67 (1H, s), 7.99-7.92 (2H, m), 7.49-7.41 (2H, m), 5.34 (1H, s), 4.62 (2H, s).

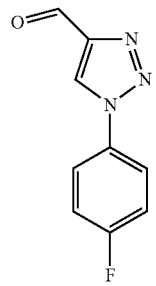 [SMILES: O=Cc1cn(-c2ccc(F)cc2)nn1]

1-(4-Fluorophenyl)triazole-4-carbaldehyde

[1-(4-Fluorophenyl)triazol-4-yl]methanol (3.80 g, 18.8 mmol) was dissolved in dry dioxane (60 mL) followed by addition of manganese(IV)oxide (13.1 g, 150 mmol). The mixture was heated at 85 C overnight. After cooling the mixture was filtered through celite and the celite was washed with additional ethyl acetate (250 mL+100 mL), ethanol (100 mL) and THF (100 mL). The combined organic phases were evaporated to yield the desired product (2.2 g, 61%, off-white solid).

$^1$H NMR (400 MHz, DMSO) 10.12 (1H, s), 9.57 (1H, s), 8.07-8.01 (2H, m), 7.54-7.49 (2H, m).

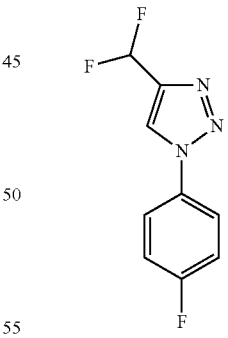

4-(Difluoromethyl)-1-(4-fluorophenyl)triazole 1-(4-Fluorophenyl)triazole-4-carbaldehyde (2.2 g, 11.5 mmol) was dissolved in dichloromethane (30 mL) and the solution was cooled to 0 C. DAST (1.95 g, 12.1 mmol) was added at 0 C and the mixture was stirred at this temperature for 1 hour followed by stirring at room temperature for 3 days. The reaction was slowly quenched with saturated $NaHCO_3$ (25 mL). Extraction with dichloromethane, drying ($MgSO_4$) and evaporation of solvent gave crude product.

The crude product was purified by column chromatography (heptane/ethyl acetate) to yield the desired product (1.85 g, 75%, brownish solid).

¹H NMR (400 MHz, DMSO) 9.25 (1H, s), 8.03-7.96 (2H, m), 7.54-7.47 (2H, m), 7.33 (1H, t, J=54.1 Hz).

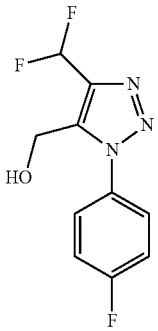

[5-(Difluoromethyl)-3-(4-fluorophenyl)triazol-4-yl]methanol

Diisopropylamine (2.27 mL, 16.2 mmol) was dissolved in dry THF (25 mL) and a nitrogen atmosphere was established. The solution was cooled to −78° C. n-Butyllithium (6.47 mL, 2.5M in hexane, 16.2 mmol) was added at this temperature over 20 minutes and the resulting mixture was stirred additionally 40 minutes at −78° C. 4-(Difluoromethyl)-1-(4-fluorophenyl)triazole was dissolved in THF (20 mL) and added to the cold solution of LDA over 20 minutes followed by stirring for 1 hour. Still at −78° C. paraformaldehyde (1.24 g, 41.2 mmol) was added in small portions and stirring was continued at −78° C. for 20 minutes before the cooling was removed and the reaction mixture was allowed to go to room temperature overnight. The reaction was quenched with water (50 mL) and extracted with ethyl acetate (3×50 mL). The combined organic phases were washed with brine (75 mL), dried (MgSO₄) and evaporated to give crude product. The crude product was purified using column chromatography (heptane/ethyl acetate) to yield the desired product with 93% purity (1.00 g, 35%, brown oil).

¹H NMR (400 MHz, DMSO) 7.81-7.75 (2H, m), 7.54-7.47 (2H, m), 7.35 (1H, t, J=53.5 Hz), 5.77 (1H, t, J=5.3 Hz), 4.64 (1H, d, J=5.0 Hz).

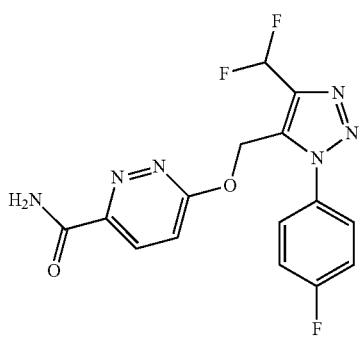 [SMILES: NC(=O)c1ccc(OCc2c(C(F)F)nnn2-c2ccc(F)cc2)nn1]

6-[[5-(difluoromethyl)-3-(4-fluorophenyl)triazol-4-yl]methoxy]pyridazine-3-carboxamide (Compound 1)

[5-(Difluoromethyl)-3-(4-fluorophenyl)triazol-4-yl]methanol (0.195 g, 0.762 mmol) was dissolved in dry DMF (5 mL) followed by addition of cesium carbonate (1.00 g, 3.05 mmol) and then 6-chloropyridazine-3-carboxylic acid amide (0.136 g, 0.800 mmol). The reaction mixture was heated at 100 C for 40 minutes and then poured into water (75 mL). The aqueous phase was extracted with ethyl acetate (4×25 mL) and the combined organic phases were washed with brine (75 mL), dried (MgSO₄) and evaporated to give crude product. The crude product was purified using column chromatography (heptane/ethyl acetate) to yield the desired product (0.208 g, 75%, off-white solid).

¹H NMR (400 MHz, DMSO) 8.32 (1H, s), 8.10 (1H, d, J=9.1 Hz), 7.83 (1H, s), 7.81-7.76 (2H, m), 7.50 (1H, t, J=53.1 Hz), 7.51-7.46 (2H, m), 7.33 (1H, d, J=9.2 Hz), 5.78 (2H, s).

Example 2

In Vitro Inhibition of ³H-Flumazenil (³H-Ro 15-1788) Binding HEK Cells Expressing the Human GABA$_A$ $\alpha_s\beta_{3*}\gamma_{2S}$ Receptor The benzodiazepine modulator unit can selectively be labelled with the antagonist ³H-flumazenil.

The affinity of ³H-flumazenil for different subunit combinations have been reported to be 1.0 nM, 1.1 nM, 1.5 nM and 0.4 nM for $\alpha_1\beta_2\gamma_2$, $\alpha_2\beta_2\gamma_2$, $\alpha_3\beta_2\gamma_2$, and $\alpha_5\beta_2\gamma_2$ receptors, respectively, and 107 nM and 90 nM for $\alpha_4\beta_2\gamma_2$ and $\alpha_6\beta_2\gamma_2$ receptors (see Sieghart; Pharmacol. Rev. 1995 47 181-234).

The pharmacology of the mutated $\alpha_5\beta_{3*}\gamma_{2S}$ GABA$_A$ receptor is similar to that of the wild type receptor with respect ³H-flumazenil binding.

Cell Cultures and Membrane Preparation

HEK-293 cell lines with stable expression of recombinant human GABA$_A$ $\alpha_5\beta_{3*}\gamma_{2s}$ receptors (plasmid H46/E9/B10) are seeded in T175 polystyrene flasks or roller bottles (1700 cm², Fisher Scientific CCI-431191), and cultured (37° C., 5% CO₂) in Dulbecco's Modified Eagle Medium (DMEM) with GlutaMAX™ supplemented with 10% fetal bovine serum and one or both of the following antibiotics: hygromycin B (50 μg/ml; γ₂ subunit) or G418 (0.5 mg/ml; α₅ subunit).

When the cultures reach confluency, the DMEM is removed and the cells are washed (10 ml for T175 flasks; 50 ml for roller bottles) once in Dulbecco's Phosphate Buffered Saline (DPBS). Following addition of DPBS to the cultures (10 ml for T175 flasks; 100 ml for roller bottles) for approximately 5 min cells are easily detached from the surface by shaking or tapping the flask gently. The cell suspension is transferred to Falcon tubes and centrifuged at 23,500×g for 10 min at 2° C. The pellet is washed once in 15 ml Tris-citrate buffer (50 mM, pH 7.1) using an Ultra-Turrax homogenizer and centrifuged at 2° C. for 10 min at 27,000×g. The washed pellet is re-suspended in 15 ml Tris-citrate buffer and frozen at −80° C. until the day of the binding experiment.

Assay

On the day of the experiment the cell membrane preparation is thawed and centrifuged at 2° C. for 10 min at 27,000×g. The pellet is re-suspended, using an Ultra-Turrax homogenizer in Tris-citrate buffer, to 15-50 μg protein per assay and then used for binding assays.

Aliquots of 500 μl cell suspension are added to 25 μl of test compound solution and 25 μl of ³H-flumazenil (1 nM, final concentration), mixed and incubated for 40 min at 2° C. Non-specific binding is determined using clonazepam (1 μM, final concentration).

All dilutions of test compounds and incubation of assay are performed in glass vials/96-vial plates. Solutions of test compounds and $^3$H-flumazenil are prepared 22× the desired final concentration. Compounds are dissolved in 100% DMSO (10 mM stock), diluted in 48% ethanol-water, and tested in triplicate in serial 1:3 or 1:10 dilutions. When screening large numbers of compounds only one concentration of each compound is tested in single wells. Reference compounds are not included routinely, but for each experiment performed total and non-specific binding is compared to data obtained during validation of the assay.

Binding is either terminated by rapid filtration onto

1) Whatman GF/C glass fibre filters using a Brandel Cell harvester, followed by 5 washes with 1 ml ice-cold buffer or onto 2) UniFilter GF/C glass fibre filter plates using a Tomtec cell harvester, followed by washing with approximately 5 ml ice-cold buffer.

The amount of radioactivity on the filters is determined by conventional liquid scintillation counting using a 1) Tri-Carb™ counter (PerkinElmer Life and Analytical Sciences) for separate large filters or 2) Topcount™ counter (PerkinElmer Life and Analytical Sciences) for 96-well filter plates. Specific binding is total binding minus non-specific binding.

Calculations 25-75% inhibition of specific binding must be obtained before calculation of an $IC_{50}$ (the concentration (µM) of the test compound which inhibits the specific binding of $^3$H-flumazenil by 50%).

The $IC_{50}$ value for a test compound is determined based on the equation:

$$B=100-(100*C^n/(IC_{50}^n+C^n))$$

where B is the binding in percentage of total specific binding; C is the concentration of test compound; and n is the Hill coefficient. For screening purposes n is set to 1. The $IC_{50}$ value is calculated from the concentration response curves by the non-linear regression method using the curve-fitting program GraphPad Prism.

The Ki value for a test compound can be calculated from the $IC_{50}$ value using the equation by Cheng and Prusoff:

$$K_i=IC_{50}/(1+L/K_d)$$

where the $K_d$ for $^3$H-flumazenil is 0.36 nM, and L is the measured concentration of $^3$H-flumazenil in the inhibition assay.

Test result from this experiment is shown in Table 1 below.

TABLE 1

In vitro inhibition of $^3$H-flumazenil

| Test compound | $K_i$ (µM) |
|---|---|
| Compound 1 | 0.087 |

Example 3

Pharmaceutical Compositions

The phenyl triazole derivative of formula (I) of the invention may be put on any desirable form of composition, and may be dosed in any desired amount. This example shows the preparation of a standard capsule formulation.

Standard Capsule Formulation

Capsules containing 1 mg active pharmaceutical ingredient (API) of formula (I) per capsule are obtained using the following composition:

| Ingredient | Function | Amount (mg/capsule) |
|---|---|---|
| API | Active ingredient | 1 |
| Starch 500 | Filler | 117 |

The calculated amount of drug substance and filler corresponding to 1 mg of active drug substance and 117 mg of filler per capsule are weighed out and dry-mixed. The blend is subsequently filled into the calculated number of capsules (preferably size 4).

Example 4

FIG. 1 shows modulation of $\alpha_5\beta_2\gamma_2$ $GABA_A$ receptor currents by the compound of formular (I) in *Xenopus laevis* oocytes. Modulatory efficacy of compound (1) (the compound of formular (I) as the free base) was determined by techniques similar to those described in Mirza et al. (*J Pharmacol Exp Ther.* 2008; 327:954-68). In brief, oocytes were injected with cRNA for human $GABA_A$ receptor subunits $\alpha_5$, $\beta_2$ and $\gamma_2$ in a 1:1:2 ratio and modulatory efficacy was evaluated by co-applications with a submaximal $EC_{5-20}$ GABA concentration (0.5 µM) termed GABAcontrol. The compound was tested in five concentrations (3.16, 0.316, 0.0316, 0.00316 and 0.000316 µM) on each oocyte starting with the lowest concentration. Background subtracted peak current amplitudes were normalized to the respective GABAcontrol current, converted to % change and depicted±S.E.M. as a function of increasing compound concentrations. Plotted datapoints were fitted to the empirical Hill equation using non-linear regression. 95% confidence intervals for maximal efficacy (Bottom) and potency (Log EC50) are derived from this fitting routine.

The invention claimed is:

1. A method of treating or alleviating a disease, disorder, or condition in a mammal comprising administering to the mammal, a therapeutically effective amount of 6-[[5(difluoromethyl)-3-(4-fluorophenyl)triazol-4-yl]methoxy]pyridazine-3-carboxamide, or a pharmaceutically acceptable salt, a polymorph, or a hydrate thereof; wherein the disease, disorder, or condition is responsive to modulation of $GABA_A$ receptors containing the α5 subunit.

2. The method of claim 1, wherein the mammal is a human.

3. The method of claim 1, wherein the disease, disorder or condition is selected from the group consisting of acute and chronic neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis, dementia caused by AIDS, psychotic disorders, substance-induced psychotic disorder, anxiety disorders, generalized anxiety disorder, panic disorder, delusional disorder, obsessive compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, and attention-deficit hyperactivity disorder.

4. The method of claim 1, wherein the disease, disorder, or condition is Alzheimer's disease, schizophrenia, positive, negative and/or cognitive symptoms associated with schizophrenia, or Down syndrome.

5. The method of claim 1, wherein the disease, disorder, or condition is Down syndrome.

6. The method of claim 1, wherein the disease, disorder, or condition is positive, negative and/or cognitive symptoms associated with schizophrenia.

* * * * *